(12) United States Patent
Geebelen (10) Patent No.: US 9,532,825 B2
(45) Date of Patent: Jan. 3, 2017

(54) INSTRUMENT AND METHOD FOR BONE FIXATION

(71) Applicant: MATERIALISE N.V., Leuven (BE)

(72) Inventor: Benjamin Geebelen, Haasrode (BE)

(73) Assignee: Materialise, NV, Leuven (BE)

( * ) Notice: Subject to any disclaimer, the term of this patent is extended or adjusted under 35 U.S.C. 154(b) by 22 days.

(21) Appl. No.: 14/504,310

(22) Filed: Oct. 1, 2014

(65) Prior Publication Data

US 2015/0018888 A1   Jan. 15, 2015

Related U.S. Application Data

(63) Continuation of application No. PCT/EP2013/057152, filed on Apr. 5, 2013.

(60) Provisional application No. 61/620,501, filed on Apr. 5, 2012.

(51) Int. Cl.

| A61B 17/88 | (2006.01) |
|---|---|
| A61B 17/56 | (2006.01) |
| A61B 17/17 | (2006.01) |
| A61B 17/80 | (2006.01) |
| B29C 67/00 | (2006.01) |
| G06F 17/50 | (2006.01) |
| A61B 17/90 | (2006.01) |

(52) U.S. Cl.
CPC .......... *A61B 17/8872* (2013.01); *A61B 17/17* (2013.01); *A61B 17/1728* (2013.01); *A61B 17/1739* (2013.01); *A61B 17/56* (2013.01); *A61B 17/808* (2013.01); *A61B 17/88* (2013.01); *B29C 67/0051* (2013.01); *G06F 17/50* (2013.01); *A61B 2017/568* (2013.01); *A61B 2017/90* (2013.01)

(58) Field of Classification Search
CPC . A61B 17/17; A61B 17/1728; A61B 17/1739; A61B 17/56; A61B 2017/568; A61B 17/808; A61B 17/88; A61B 17/8872; A61B 2017/90

See application file for complete search history.

(56) References Cited

U.S. PATENT DOCUMENTS

| 7,604,638 | B2 * | 10/2009 | Jacene | A61B 17/808 606/71 |
|---|---|---|---|---|
| 8,728,082 | B2 * | 5/2014 | Fritzinger | A61B 17/80 606/286 |
| 9,005,207 | B2 * | 4/2015 | Dodds | A61B 17/155 606/87 |
| 9,161,796 | B2 * | 10/2015 | Chiodo | A61B 17/8061 |
| 2005/0283155 | A1 | 12/2005 | Jacene | |
| 2007/0118243 | A1 | 5/2007 | Schroeder | |
| 2008/0161815 | A1 | 7/2008 | Schoenfeld | |
| 2009/0163922 | A1 | 6/2009 | Meridew | |
| 2009/0312801 | A1 | 12/2009 | Lemoine | |
| 2011/0087332 | A1 | 4/2011 | Bojarski | |
| 2011/0106169 | A1 | 5/2011 | Zalenski | |

FOREIGN PATENT DOCUMENTS

| WO | 2012/154407 A2 | 11/2012 |
|---|---|---|
| WO | 2013/041618 A1 | 3/2013 |

* cited by examiner

*Primary Examiner* — Larry E Waggle, Jr.

(57) ABSTRACT

Described herein are guiding instruments for use in surgical procedures involving the positioning of a bone plate. Furthermore methods for the manufacture of such instruments and methods for positioning a bone plate are also provided.

10 Claims, 6 Drawing Sheets

INSTRUMENT AND METHOD FOR BONE FIXATION

CROSS-REFERENCE TO RELATED APPLICATIONS

This application is a continuation under 35 U.S.C. §120 of International Application No. PCT/EP2013/057152, filed Apr. 5, 2013 (and published in English on Oct. 10, 2013 by the International Bureau as International Publication No. WO2013/150124), which claims priority to U.S. Provisional Application No. 61/620,501, filed Apr. 5, 2012. The entire contents of each of the above-referenced patent applications is hereby incorporated by reference.

BACKGROUND OF THE INVENTION

Field of the Invention

Described herein are guiding instruments for use in surgical procedures involving the positioning of a bone plate. Furthermore methods for the manufacture of such guiding instruments and methods for positioning a bone plate are also provided.

Description of the Related Technology

In complex surgeries like corrective osteotomies or acute trauma surgeries, the surgeon wants to correct a malunion, a congenital deformity or the like, to relieve pain or to improve the functionality of a part of the patient anatomy. The quality of the end result highly depends on the accuracy achieved during the surgical procedure.

For a number of years, the combination of virtual pre-operative planning and patient-specific surgical instruments has been available for performing complex orthopedic surgeries. This combination allows the surgeon to meticulously plan the surgery in advance on a virtual 3D model, and then execute this planning in the operating room by using patient-specific surgical instruments, which are unique to the patient and the planned surgery. The patient-specific instruments typically fit on a part of the patient anatomy and guide the surgeon in making osteotomies, in drilling and placing pins and screws.

For corrective osteotomies, the patient-specific instruments typically allow the surgeon to accurately pre-drill holes for the screws that will hold an osteosynthesis plate and to accurately make the osteotomy according to the pre-operative planning. The reduction of the bone fragments is then performed by attaching the osteosynthesis plate using the pre-drilled screw holes. Various types of osteosynthesis plates are available, such as standard compression plates, patient-specific plates and locking plates.

When using standard compression plates, the pre-operative planning should be made such that the plate contacts the bone. However, in the case of corrective osteotomies, one is typically dealing with abnormal anatomy, such that a stable contact between the plate and the bone fragments cannot always be guaranteed.

An alternative is to use a patient-specific plate. Such a plate can be designed to fit the patient anatomy in a stable manner. However, patient-specific implants are expensive to engineer and manufacture. Moreover, the plate can cause bone necrosis if the fit is too snug.

For these reasons, many surgeons prefer using locking plates and screws. In such systems, the screw holes provided on the plate and the screw heads are threaded, such that the screws can interlock with the plate. This allows attachment of the osteosynthesis plate without it making full or even any contact with the bone. However, the use of locking plates also has certain disadvantages. For example, without a stable contact between plate and bone, it is impossible for the surgeon to guarantee the same relative end positions of plate and bone fragments that were planned pre-operatively. Moreover, it is difficult to position the screws in the pre-operatively planned direction, even with pre-drilled holes for the screws. Indeed, although pre-drilling allows the surgeon to accurately find the correct entry point through the cortical bone, screws can easily divert from the pre-drilled tunnel in the trabecular bone. This is particularly problematic for angularly stable locking plates.

Accordingly, there is a need for improved methods for performing a corrective osteotomy, and for positioning of bone plates in general.

SUMMARY

Described herein are guiding instruments for use in surgical procedures involving the positioning of a bone plate. Additional embodiments further provide methods for the manufacture of such guiding instruments and methods for positioning a bone plate.

According a first aspect patient-specific guiding instruments are provided for positioning a bone plate on at least one of two or more bone fragments, which ensure the accurate positioning of the bone plate on the bone fragments and thus ensure optimal repositioning of the bone fragments relative to each other according to a pre-operatively determined plan. More particularly, the guiding instruments for positioning a bone plate may comprise one or more patient-specific anatomy engagement surfaces or anatomy contact points corresponding to at least a part of at least one of the two or more bone fragments; and one or more plate engagement features for connecting the guiding instrument to the bone plate.

In particular embodiments, the guiding instruments are for positioning a bone plate on two or more bone fragments.

In particular embodiments, the guiding instruments comprise one or more locking features, optionally incorporated into one or more of the plate engagement features, for releasably locking the guiding instrument onto the bone plate.

In further embodiments, at least one of the locking features of the guiding comprises a locking feature which locks the guiding instrument onto the bone plate. Such a locking feature can be a dedicated feature, such as a snap-fit system; or can be a feature which may have other functions. For instance, in particular embodiments, the locking feature is a threaded hole.

In certain embodiments, the guiding instrument further comprises one or more drill guides for guiding a screw or a drill.

In particular embodiments, at least one plate engagement feature comprises a structure extending over at least part of the circumference of the bone plate. More particularly the structure extending over the bone plate may comprise a recess fitting the bone plate. In certain embodiments, at least one of the plate engagement features is shaped to engage onto one or more screw holes provided on the bone plate.

In particular embodiments, the guiding instruments as described herein, comprise two or more detachable guide parts, which when fit together over the bone plate form the guiding instrument. Typically in these embodiments, at least one of the guide parts comprises one or more plate engagement features for connecting the guide part to the bone plate; moreover, in these embodiments, at least one of the guide parts comprises one or more patient-specific anatomy engagement surfaces or anatomy contact points corresponding to at least a part of one of the two or more bone fragments on which the bone plate is to be fitted; and each guide part comprises one or more connecting features for uniquely connecting the guide parts to each other. Such connecting features are typically selected from interlocking features, a snap-fit system, a dovetail system, a pinned system and a magnetic system.

In particular embodiments, the guiding instruments as described herein are manufactured at least partially via additive manufacturing. Indeed, this technology easily allows the incorporation of patient-specific features into the guiding instrument which correspond to features determined based on pre-operative planning.

In a further aspect, combinations of a bone plate and a patient-specific guiding instrument as described herein are provided. The bone plate may be a standard bone plate, or may be tailored to the specific requirements of the patient.

In yet a further aspect, methods are provided for positioning a bone plate on at least one of two or more bone fragments. In particular embodiments, the methods are for positioning a bone plate on two or more bone fragments. These methods involve the use of a guiding instrument for positioning a bone plate as disclosed herein. Thus, these methods typically comprise, the steps of: (i) providing a patient-specific guiding instrument as described herein and (ii) connecting it to a bone plate. The methods further comprise the steps of (iii) positioning the guiding instrument connected to the bone plate in step (ii), on at least one of the bone fragments via one or more anatomy engagement surfaces and/or anatomy contact points; the step of (iv) fixing the bone plate onto one or more of the bone fragments; and (v) disengaging the guiding instrument from the bone plate. In particular embodiments, the envisioned methods may comprise the step of fixing the guiding instrument to one or more of the bone parts after step (iii), such that step (v) further comprises disengaging the guiding instrument from the one or more bone fragments. Further particular embodiments of the methods for positioning a bone plate on one, two or more bone fragments will be determined by the specific features of the guiding instruments described herein.

In yet a further aspect, the present disclosure provides methods for making a patient-specific guiding instrument for positioning a bone plate on at least one of two or more fragments of a bone. In further embodiments, the guiding instruments are for positioning a bone plate on two or more fragments of a bone. These methods typically involve designing a guiding instrument so as to fit precisely onto one or more predetermined areas of at least one of the bone fragments, such that when the bone plate is connected to the bone fragments, the bone fragments are correctly positioned. More particularly, the methods for making the guiding instruments disclosed herein comprise the steps of: (a) obtaining a two-dimensional (2D) or three-dimensional (3D) model of at least a part of the bone; (b) obtaining a preoperative planning model corresponding to an envisioned repair of the bone or an envisioned result of an osteotomy on the bone; (c) generating a patient-specific guiding instrument based on the information obtained in steps (a) and (b), the guiding instrument comprising: one or more patient-specific anatomy engagement surfaces or anatomy contact points corresponding to at least a part of one or both of the bone fragments; one or more plate engagement features for connecting the guiding instrument to the bone plate, wherein the guiding instrument is designed such that correct positioning of the patient-specific anatomy engagement surfaces or contact points on the bone fragments ensures correct positioning of the bone plate connected to the guiding instrument according to the preoperative plan.

Again, the different embodiments of the method for making the guiding instruments may be determined by the different embodiments of the guiding instruments envisioned herein. In particular embodiments, the methods are used for the manufacturing of guiding instruments by additive manufacturing.

BRIEF DESCRIPTION OF THE DRAWINGS

The following description of the figures of specific embodiments as described herein is merely exemplary in nature and is not intended to limit the present teachings, their application or uses. Throughout the drawings, corresponding reference numerals indicate like or corresponding parts and features.

In the figures, the following numbering is used: 1—bone plate; 2, 3—guide part of a guiding instrument; 4—screw; 5,5'—bone fragment; 6—anatomy engagement surface; 7—plate engagement feature; 8, 9—connecting feature; 10—locking features; 12—hinge; 13—snap-fit element; 14—recess for snap-fit element; 15—screw hole; 20—Dynamic Compression Plate; 21—Limited Contact Dynamic Compression Plate.

DETAILED DESCRIPTION OF CERTAIN INVENTIVE EMBODIMENTS

While certain embodiments as provided herein will be described, these embodiments will be presented by way of example only, and are not intended to limit their scope. Indeed, the novel embodiments described herein may be embodied in a variety of other forms; furthermore, various omissions, substitutions and changes in the form of the embodiments described herein may be made without departing from the spirit of the description. The accompanying claims and their equivalents are intended to cover such forms or modifications as would fall within the scope and spirit of the description.

As used herein, the singular forms "a", "an", and "the" include both singular and plural referents unless the context clearly dictates otherwise.

The terms "comprising", "comprises" and "comprised of" as used herein are synonymous with "including", "includes" or "containing", "contains", and are inclusive or open-ended and do not exclude additional, non-recited members, elements or method steps. The terms "comprising", "comprises" and "comprised of" when referring to recited components, elements or method steps also include embodiments which "consist of" the recited components, elements or method steps.

Furthermore, the terms first, second, third and the like in the description and in the claims, are used for distinguishing between similar elements and not necessarily for describing a sequential or chronological order, unless specified. It is to be understood that the terms so used are interchangeable under appropriate circumstances and that the embodiments described herein are capable of operation in other sequences than described or illustrated herein.

Reference throughout this specification to "one embodiment" or "an embodiment" means that a particular feature, structure or characteristic described in connection with the embodiment is included in at least one embodiment as described herein. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to a person skilled in the art from this disclosure, in one or more embodiments. Furthermore, while some embodiments described herein include some but not other features included in other embodiments, combinations of features of different embodiments are meant to be within their scope, and form different embodiments, as would be understood by those in the art. For example, in the appended claims, any of the features of the claimed embodiments can be used in any combination.

The values as used herein when referring to a measurable value such as a parameter, an amount, a temporal duration, and the like, is meant to encompass variations of +/−10% or less, preferably +/−5% or less, more preferably +/−1% or less, and still more preferably +/−0.1% or less of and from the specified value, insofar as such variations are appropriate to perform in the disclosed embodiments. It is to be understood that each value as used herein is itself also specifically, and preferably, disclosed.

The recitation of numerical ranges by endpoints includes all numbers and fractions subsumed within the respective ranges, as well as the recited endpoints.

All documents cited in the present specification are hereby incorporated by reference in their entirety.

Unless otherwise defined, all terms used in the disclosure, including technical and scientific terms, have the meaning as commonly understood by one of ordinary skill in the art. By means of further guidance, definitions for the terms used in the description are included to better appreciate the present teaching. The terms or definitions used herein are provided solely to aid in the understanding of the disclosure.

The term "defective bone" refers to any bone in the body a human or animal patient for which a surgical procedure is envisioned involving the positioning of a bone plate. Possible bone defects include, but are not limited to a fracture, a malunion and a congenital deformity.

In general, according to certain embodiments, guiding instruments and methods of generating patient-specific guiding instruments for use during surgical interventions requiring the installation of a bone plate, for example a corrective osteotomy, are provided. The patient-specific guiding instruments can be made to ensure the fitting of a bone plate according to a pre-operative plan. The guiding instruments can be designed to fit securely onto a bone plate (which can be a standard bone plate) and specifically onto one, two or more bone fragments, such that when the guiding instrument is correctly fitted onto the bone fragment(s), the plate is also correctly positioned. This is ensured by designing the guiding instruments by making use of patient-specific features based on the pre-operative planning.

In a first aspect, one embodiment provides methods for generating patient-specific guiding instruments for positioning a bone plate on at least one of two or more parts of a bone or bone fragments.

A bone plate (or osteosynthesis plate) is used for fixing two or more bone fragments according to a pre-operative plan. The term "bone fragments" as used in the context of the present disclosure refers to partially or completely separated parts originating from one bone. Typically, bone plates are used in orthopedics for internal fixation of bones, typically after fractures or osteotomies. An osteotomy is a surgical intervention involving cutting of a bone in order to shorten the bone, lengthen it or change its alignment. By fixing the bone plate to the bone fragments, the bone plate ensures that the two or more bone fragments are fixed in position relative to each other to assist the healing and/or to stabilize damaged or weakened bones or portions of the bone.

Bone plates often, but not necessarily have a longitudinal shape in order to extend over part of each of the bone fragments and optionally to span a gap between two bone fragments or a stretch of weakened bone. For example, the bone plates may have an aspect ratio (i.e. the length divided by the width) above 2, 3, 5, 8 or more. The bone plate may have a straight or curved shape, depending on the bone (parts) on which it is to be positioned.

Bone plates further have a rigid structure such that, after fixation to the bone or bone fragments, they can maintain these in position even under stress conditions. The bone plate may be a locking plate, i.e. a bone plate comprising one or more threaded holes for receiving a threaded screw. Typically, the bone plate is a standard (i.e. not patient-specific) plate, more particularly a standard metallic plate. The standard bone plates may be anatomical bone plates, which are specifically designed to be used in a specific region of the body. For example, the bone plate may be a (T-shaped) radius plate, for positioning on a radius bone. Alternatively, the bone plate may be a generic plate, which is not specific to a certain body region. Generic bone plates often have a straight shape.

Figure 8:
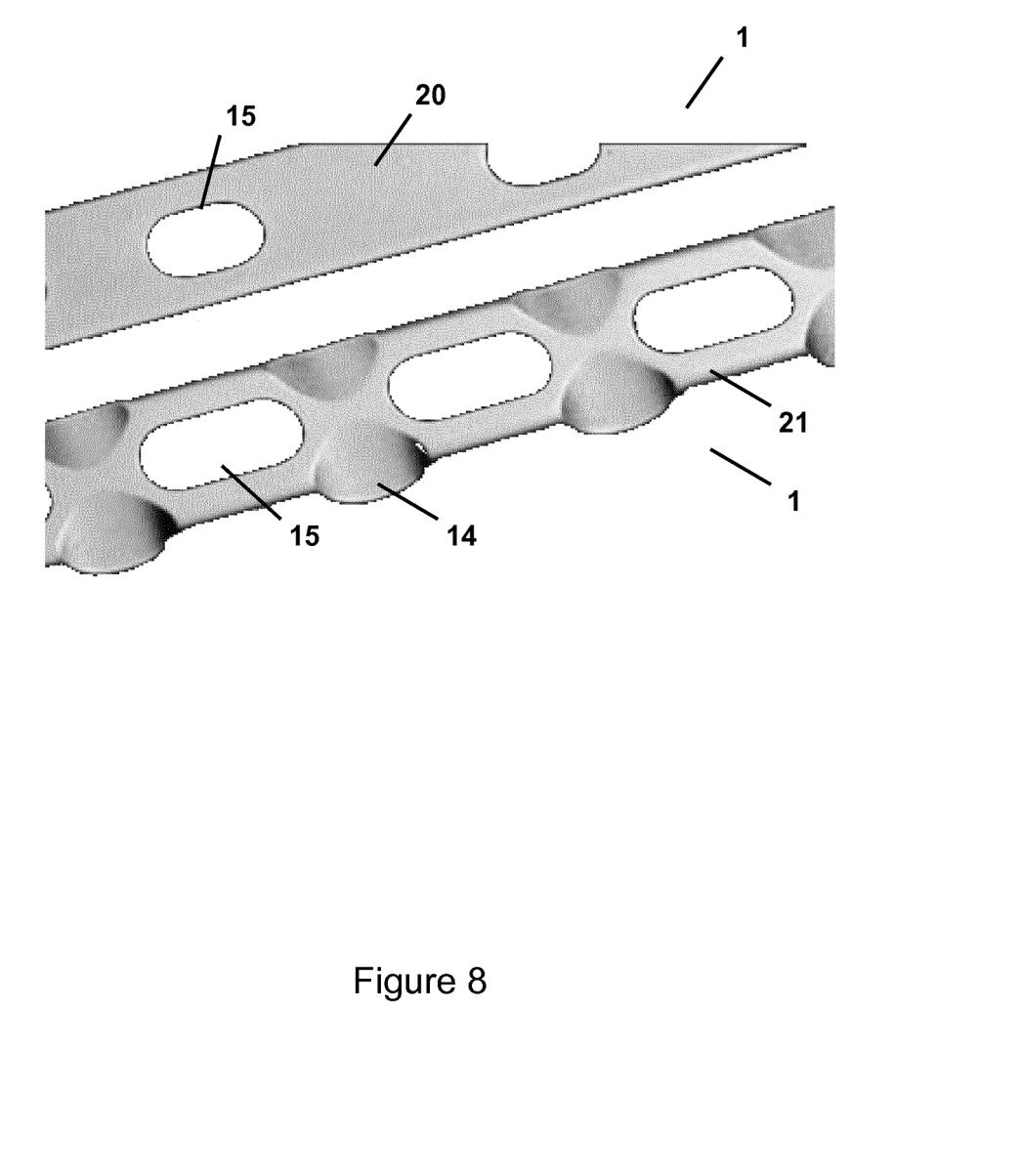
FIG. 8 illustrates two bone plates from the prior art: a Dynamic Compression Plate (20) and a Limited Contact Dynamic Compression Plate (21).

A variety of standard bone plates are, among others, provided by Synthes Holding AG. FIG. 8 provides an illustration of some particular bone plates which may be used in the present context. A dynamic compression plate (DCP) is a typical bone plate which additionally exerts dynamic pressure between the bone fragments to be transfixed. For regular bone plates, dynamic compression can be achieved by attaching a tension device to the bone plate. Dynamic compression plates are provided with screw holes that are shaped with an angle of inclination on one side away from the center of the plate. When tightened, the screw head slides down the inclination, causing movement of the bone fragment relative to the plate, result in a dynamic compression. A Limited Contact dynamic compression plate. (LC-DCP) is a dynamic compression plate with limited contact to the underlying bone which minimizes disruption in periosteal capillary network and thus in the fracture zone. The limited contact is achieved by providing recessions on the proximal side of the bone plate, thereby minimizing bone-plate contact and providing an even distribution of strength.

The methods for generating patient-specific guiding instruments can typically involve ensuring that the guiding instrument can be attached to the bone plate and can be positioned on the bone in order to ensure correct positioning of the bone plate.

The terms "positioning" and "fixing" as used herein, when referring to positioning or fixing of a bone plate onto one or more bone parts, does not necessarily imply that the bone plate itself contacts the bone part(s). Indeed, in particular embodiments, the bone plate may be positioned on a bone fragment via one or more screws, without direct contact between the bone plate and the bone fragment.

In particular embodiments, the bone plate will span a section or weakened area between two or more bone fragments, such that the bone plate is fixed by different screws to different bone fragments. In alternative embodiments, the bone plate will ensure the correct positioning of screws whereby the screws ensure the fixing of the two or more bone fragments relative to each other. In these embodiments, the bone plate may be fixed by one or more, typically two or more screws which each contact two or more bone fragments. In these embodiments, the guiding instrument will typically contact only one bone part (as detailed below).

As will be apparent form the present description, the term "positioning" as used herein, when referring to positioning of a guiding instrument on one or more bone parts, typically implies that the guiding instrument contacts, more particularly specifically mates with at least one of those bone parts.

Indeed, in order to ensure correct positioning of the guiding instrument relative to the bone fragments according to the envisioned position of the bone plate, the guiding instrument is provided with specific features which can be specifically mated with one or more bone fragments. These features are based on features of the bone fragments and the position of these features on the guiding instrument is determined by the preoperative planning. Thus, in certain embodiments, a 2D or 3D model of a bone defect or envisioned osteotomy can be generated based on one or more images thereof and generating a 2D or 3D model of the envisioned repair of the bone defect or result of the osteotomy. Based thereon, a guiding instrument for positioning a bone plate is generated, which guiding instrument contains features matching with or corresponding to at least part of the surface of one or more of the bone fragments in their envisioned position upon repair of the bone. Typically, the guiding instrument comprises a guide body (consisting of one or more parts) which comprises one or more patient-specific anatomy engagement surfaces or anatomy contact points incorporated therein. In particular embodiments, e.g. where the bone plate is a bone plate which spans a separation or weakened area between two or more bone fragments, the guiding instrument may be designed to be positioned specifically onto two or more bone fragments. In these embodiments, the guiding instrument may comprise features matching with or corresponding to at least part of the surface of two or more and/or each of the bone fragments which are to be joined together. This will aid in the correct positioning of the bone fragments relative to each other. However, in particular embodiments, the bone plate may be used to secure screws which connect two or more bone fragments. In these embodiments, the guiding instrument may contain one or more features matching with or corresponding to at least part of the surface of only one of the bone fragments. The presence of these features on the guide body, ensures correct positioning of the guiding instrument (and thus the plate connected therewith, as detailed below) during use.

Accordingly, in one embodiment, methods for generating patient-specific guiding instruments are provided comprising the steps of: (a) generating a 2D or 3D model of at least a part of a bone; and (b) designing, based on the 2D or 3D model generated in step (a), a preoperative planning model corresponding to an envisioned repair of the bone or an envisioned result of an osteotomy on the bone.

Based on this information, the patient-specific guiding instrument can be generated. Indeed, the envisioned repair of the bone or envisioned result of an osteotomy will determine the desirable position of the bone plate. Based thereon, patient-specific surfaces can be determined in the area surrounding the envisioned position of the bone plate which can be used to position the guiding instrument, as will be detailed below. The guiding instrument can then be designed to comprise a body (consisting of one or more parts) which incorporates the patient-specific surfaces and optionally additional features for connecting to the bone plate (as will be detailed below).

In particular embodiments, the 2D or 3D model of at least part of a bone and the preoperative planning model corresponding to the envisioned repair of the bone or an envisioned result of an osteotomy on the bone are generated separately and this information is provided such that a patient-specific guiding instrument can be generated. In alternative embodiments, the envisioned methods will include steps (a) and (b) recited above and will further include step (c) comprising generating a patient-specific guiding instrument based on the information obtained in steps (a) and (b). These different steps will be described further below.

As detailed above, certain embodiments of the methods described herein provide for the use of a 2D or 3D model of a defective bone or a part thereof. The model can be obtained based on 2D or 3D images of the defective bone. In particular embodiments, this includes the step of taking images of the bone or bone defect. The images may be any type of image that can be used to create a 2D or 3D image or model of the envisioned repair of the bone or result of the osteotomy.

In particular embodiments, the images are 2D or 3D images. The images can be taken using any type of imaging apparatus or imaging technique which allows imaging or scanning the defective bone in an accurate manner. These may include equipment such as cameras and scanners for industrial, household or medical use. In particular embodiments the imaging techniques and appliances used are typical medical imaging tools such as, but not limited to radiography, X-ray, ultrasound or fluoroscopy for 2D images and computer tomography (CT) scans, magnetic resonance imaging (MRI) scans or ultrasound for 3D images. It is noted that from a combination of 2D images a 3D model can be constituted (according to U.S. 61/579,927, which is incorporated herein by reference). A summary of medical imaging has been described in "Fundamentals of Medical Imaging", by P. Suetens, Cambridge University Press, 2002.

The term "medical imaging" as used herein refers to techniques and processes used to create images of the human or animal body (or parts and function thereof), typically for clinical purposes (medical procedures seeking to reveal, diagnose or examine disease) or medical science (including the study of normal anatomy and physiology).

In further embodiments, a preoperative planning model corresponding to the envisioned repair of the bone defect or the envisioned result of the osteotomy can be designed based on the 2D or 3D model of the defective bone or part thereof. Indeed, the 2D or 3D model allows a detailed analysis of the bone defect or osteotomy, and allows the reconstitution of the bone fragments to their original position and/or the provision of the desired repair of the defect or osteotomy.

In particular embodiments, this step involves performing virtual surgery on the defective bone to identify the defect site and determining the shape and/or form parameters of the defect or of the structure necessary to fix the defect. Based thereon, a preoperative planning model, i.e. a model corresponding to the envisioned repair of the bone defect or osteotomy is generated. This model can be obtained in a number of ways, including by manual designing based on anatomical knowledge. This involves determining the optimal position of the remaining elements relative to each other. Where the bone is a long bone, typically, the defect or osteotomy will generate two or more bone fragments which need to be fixed in a specific position relative to each other. In other embodiments, such as fractures of the skull, the optimal position of multiple pieces may need to be determined.

The pre-operative planning typically further comprises selecting a bone plate and defining the desired relative position of the bone fragments and the bone plate. In particular embodiments, the bone plate is selected from a database of standard bone plates based on parameters such as bone type, bone size, defect type, etc. Typically, the bone plate is a structure comprising two or more screw holes for fixation to two or more bone fragments.

According to certain methods described herein, a patient-specific guiding instrument can be generated based on the model corresponding to the envisioned repair of the bone defect or envisioned osteotomy obtained as described above.

Figure 3:
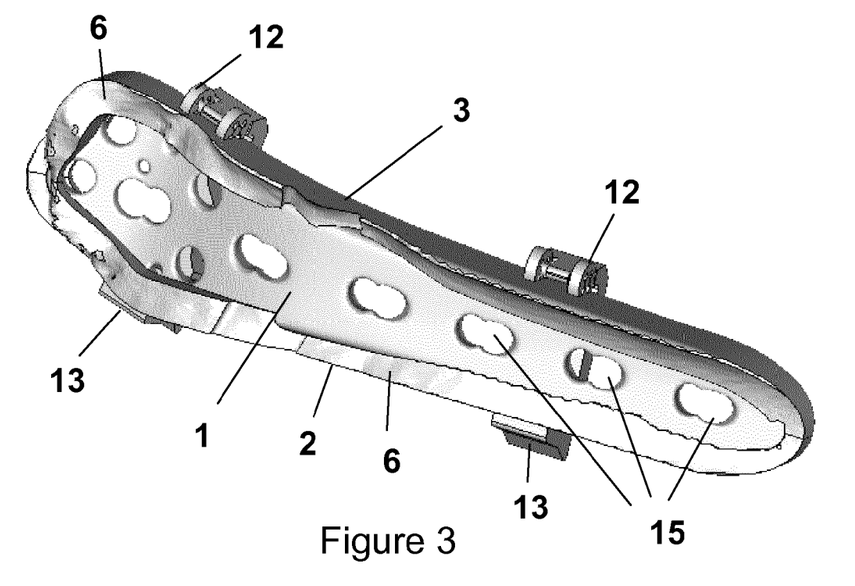
FIG. 3 illustrates a guiding instrument (2, 3) according to a particular embodiment described herein, connected to a bone plate (1).
Figure 4:
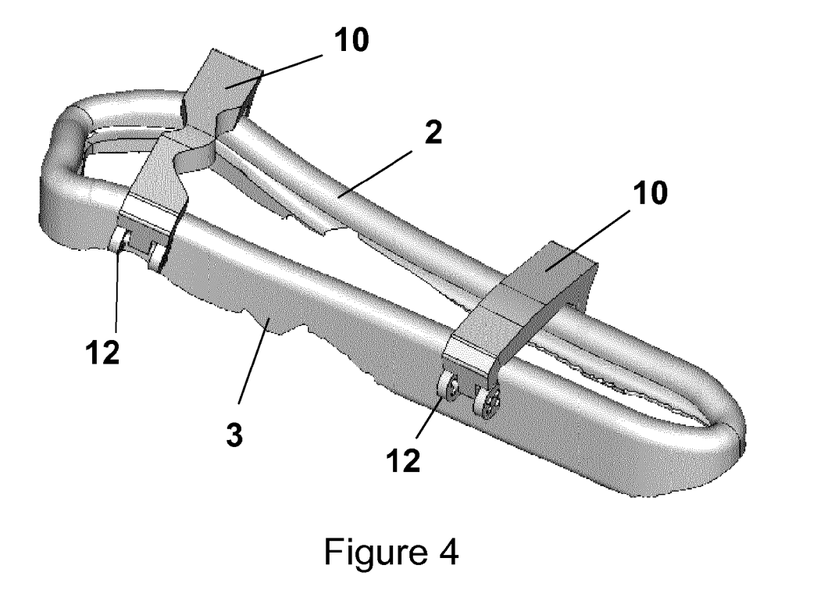
FIG. 4 illustrates a guiding instrument (2, 3) according to a particular embodiment described herein.

The guiding instrument is made to be patient-specific in that it comprises one or more patient-specific features matching or corresponding to at least a part of the surface of at least one of two or more bone fragments. Typically, these bone fragments are from the defective bone. This ensures a snug, unique and pre-operatively planned fit of the guiding instrument on the surface of the bone fragments. In some embodiments, the guiding instrument contains features which correspond to features of only one of the bone fragments. In other embodiments, the guiding instrument will comprise features corresponding to each bone fragment envisioned to be fixed by the bone plate. These features will be selected such that they are located in a region of the bone fragment which is located in the vicinity of the envisioned position of the bone plate. Typically, the surface of the bone fragment selected for the design of a patient-specific anatomy engagement surface or one or more anatomy contact points in the guide is located, in the envisioned repair model, near to the periphery of the position of the bone plate. Typically, the design of the guiding instrument will involve the design of a guide body which provides support for the one or more patient-specific anatomy engagement surfaces or one or more anatomy contact points and fixation of the bone plate thereto. The shape of the guide body is not critical but will typically be limited in size to allow its use in a limited surgical window. In particular embodiments the guide body consists of one or more parts which form a sleeve around the circumference of bone plate. The sleeve can be a solid structure as illustrated in FIGS. 3 and 4, but can also be a grid-like structure connecting the patient-specific contact surfaces or contact points.

Thus, the guiding instrument is designed based on the models obtained as described above such that, when the guiding instrument is positioned on the one or more bone fragments using these patient-specific features, the relative position of the bone fragments is the pre-operatively planned position. The model will allow the identification of areas on the bone fragments (typically in the vicinity of the defect) that are suitable for positioning the guiding instrument on the bone fragments.

The patient-specific features provided on the guiding instrument can be selected from patient-specific anatomy engagement surfaces (which match a specific surface structure on the bone, with or without cartilage or other soft tissues) and/or combinations of specifically placed anatomy contact points such as pins (corresponding to a specific shape of the bone), etc.

In particular embodiments, the guiding instrument as described herein further comprises positioning means which aid the positioning of the guiding instrument onto the bone part(s). The positioning means that are provided onto the guiding instrument may be any means which allow a first attachment of the guiding instrument onto one or more bone fragments. In particular embodiments, these positioning means are non-threaded appendages such as, but not limited to pins, pegs or hooks. However, such positioning means can also be provided as holes for fitting of a pin, peg or hole. In certain embodiments, the guiding instrument may comprise at least one positioning means which is provided on a part of the guiding instrument envisioned to be positioned on one of the bone fragments. In particular embodiments, more particularly where the guiding instrument is envisioned to be positioned onto two or more bone fragments, the guiding instrument may comprise at least two positioning means, one on each bone fragment. Where the guiding instrument is envisioned to span over a bone defect or weakened area between two or more bone fragments, one positioning means may be located on one bone part adjacent the bone defect or cut and another positioning means may be located on another bone part adjacent to the bone defect or cut.

In particular embodiments, the surgical methods involving the use of a guiding instrument as described herein comprising positioning means may require drilling one or more holes into the bone part(s), for receiving the positioning means, or pins or the like for interaction with the positioning means, prior to the placement of the guiding instrument. Drilling of the holes may be ensured by using a guide and may be done according to the pre-operatively planned position of the guiding instrument and bone plate.

The guiding instrument is further designed such that it can releasably hold or be releasably connected to a bone plate. Thus, the guiding instrument comprises one or more plate engagement features capable of connecting the guiding instrument to at least a part of the bone plate. The one or more plate engagement features are positioned in the guiding instrument such that, when connected to the corresponding position on the bone plate, they can ensure a fixed position of the bone plate in the guiding instrument.

In particular embodiments this connection is ensured over an extended region of the bone plate by way of an engagement surface. Various types of engagement surfaces are envisioned. In particular embodiments, the guiding instrument comprises a body (consisting of one or more parts) with a recess such as a groove, matching the circumference of the bone plate or parts thereof, such that the guiding instrument can surround and hold the bone plate. In particular embodiments, the guiding instrument consists of two parts which, when connected, can form a sleeve around the bone plate, whereby the bone plate fits into a groove extending along the inner surface of the sleeve. Thus, in particular embodiments, the guide body consists of one or more parts forming a closed sleeve structure (or which can be connected to form a closed sleeve structure).

In certain embodiments, the guiding instrument comprises several tabs for holding the bone plate. The tabs may be arranged at different positions around the circumference of the bone plate. Additionally or alternatively, one or more plate engagement features may be designed to grip the bone plate in one or more of the (screw) holes provided in the bone plate. In certain embodiments, the bone plate comprises one or more recesses onto which can interact with the one or more plate engagement features present on the guide. Additionally or alternatively, one or more plate engagement features may be specifically designed to grip the bone plate in one or more of the recesses provided on the bone plate. For instance, where the bone plate is a Limited Contact Dynamic Compression Plate (LC-DCP), the guiding instrument as described herein may comprise one or more plate engagement features designed to grip onto and/or behind the recesses, thereby allowing the guiding instrument to secure the bone plate into a fixed position. In particular embodiments, the plate engagement features provide in a protrusion with an overhang or undercut between 0.2 mm and 5 mm, in particularly, between 0.5 mm and 2.5 mm, and more particularly about 1 mm.

Thus, the guiding instrument is designed such that it can be reversibly connected to a bone plate, and be positioned on one, two or more bone fragments in a unique way, more particularly according to a pre-operatively planned configuration. Consequently, the guiding instrument is designed such that when the guiding instrument holds or is connected to the bone plate via the plate engagement features and is positioned on the bone fragments via the patient-specific features, the bone fragments and the bone plate are in the preoperatively planned position.

In particular embodiments, the guiding instrument may be designed as a single part comprising a body with patient-specific features and a plate engagement feature as described above incorporated therein. In other embodiments, the body of the guiding instrument comprises two or more detachable guide parts, wherein each of the guide parts comprises one or more plate engagement features and at least one of the guide parts comprises one or more patient-specific features. Typically the guiding instrument will contain two guide parts, which can be locked together around the bone plate. The provision of more than one guide part can facilitate connecting the guiding instrument to the bone plate, and particularly facilitates the subsequent disconnection of the guiding instrument from the bone plate after fixation of the bone plate to the bone fragments. In certain embodiments, each of the guide parts comprises one or more patient-specific features. Optionally, the two or more guide parts may each comprise one or more connecting features for the assembly of the guide parts of the guiding instrument. Typically, the connecting features from the guide parts comprise pairs of matching surfaces. In particular embodiments, the connecting features may comprise pairs of matching protrusions and recesses. This helps to maintain the detachable guide parts in a fixed relative position during use. Thus in particular embodiments, the guide parts, when fit together form a continuous sleeve, which can be positioned around the bone plate so as to fix the bone plate therein. In other embodiments, the plate engagement features are not continuous but are positioned at discrete locations around the bone plate and are or can be interconnected in a fixed position relative to each other.

In certain embodiments, the guide parts comprise one or pairs of connecting features forming a system selected from interlocking features, a snap-fit system, a dovetail system, a pinned system and a magnetic system.

As described above, the guiding instrument comprises one or more plate engagement features which allow the guide to be connected to the bone plate. In particular embodiments, the combination of plate engagement features and connecting features will ensure that the guiding instrument can be releasably connected to the bone plate. However, in other embodiments, the guiding instrument may further comprise locking features which further lock the bone plate into the guiding instrument in a releasable way. This may further ensure a tight fit of the bone plate within the guiding instrument during use and/or may facilitate the release of the bone plate after use. In further embodiments, the locking features are an integral part of the engagement features. However, additionally or alternatively, the guiding instrument may be provided with one or more dedicated locking features for releasably locking the guiding instrument to the bone plate.

In particular embodiments, the locking feature can correspond to a snap-fit system, securing two guiding parts into place around the bone plate. In further embodiments, the locking feature can be an element which engages into the screw holes of the bone plate via a snap-fit mechanism. In certain embodiments, the locking features can comprise a lever element which is hinged at one end to a first guide part of the guiding instrument, whereby the other end of the lever element is shaped to engage with a matching feature such as a recess or protrusion present on a second guide part of the guiding instrument. Preferably, the lever element and the matching feature form a snap-fit system. In particular embodiments, the guiding instrument comprises a snap-fit locking feature can correspond and the bone plate comprises one or more recesses onto which the snap-fit locking feature can engage. In particular embodiments the bone plate is a Limited Contact Dynamic Compression Plate comprising recesses.

Additionally or alternatively, one or more locking features may comprise a threaded hole. This allows the surgeon to screw the guiding instrument on the bone plate it holds via one or more screw holes provided on the bone plate, thereby releasably locking the bone plate onto the guiding instrument. Thus, in certain embodiments, the guiding instrument comprises one or more threaded holes with a similar diameter and thread as one or more screw holes provided in a corresponding position in the bone plate. The locking feature(s) may be selected from a database of standard elements, or may be designed together with other features of the guiding instrument. In particular embodiments, the shape of the locking feature is adapted to avoid interference with the passageway of one or more screws required for fixing the bone plate to the bone fragments.

In additional embodiments, the guiding instrument can be fixed to one or more of the bone fragments temporarily, such that the relative position of the bone fragments and the guiding instrument with the bone plate is locked. Such fixation may be obtained via screws, wires and pins such as Kirschner wires and the like. Accordingly, in particular embodiments, the surgical guides may comprise one or more fixation features such as holes, which allow for temporary fixation of the guiding instrument onto the bone fragments, for example using screws, wires or pins. Additionally or alternatively, one or more fixation features may be positioned via one or more holes provided in the bone plate.

Thus, according to particular embodiments, the methods described herein may further comprise determining the optimal position and/or orientation of one or more fixation features for fixing the guiding instrument onto the bone and designing the guiding instrument with a fixation feature for locking onto the bone. In particular embodiments, the fixation feature is a screw hole.

In particular embodiments, the guiding instrument can comprise one or more drill guides for guiding a screw and/or a drill. In particular embodiments, these drill guides may be removable from the guiding instrument.

In particular embodiments, one or more drill guides for screws comprising a head and an elongated body having a different diameter may comprise: an introducer shaft which engages with the head of the screw; and a guide system, positioned at least in part inside the introducer shaft, wherein the guide system engages with part of screw device such that the screw is prevented from passing through the introducer shaft unless the it passes through the guide system according to a predefined axis. Such a drill guide allows accurate placement of a locking screw, even when the screw head has a larger cross section than the elongated body. Reference is made in this regard to the systems described in U.S. 61/580,781, which are incorporated by reference herein.

In particular embodiments, the guiding instruments described herein comprise a body having a structure (or different guide parts forming a structure) which contacts the bone plate partially or completely around its circumference. However, other shapes are also envisioned. Further, the structure of the guiding instrument can be such that removal of the guiding instrument is required prior to screwing the last screws into the bone plate and the bone. This is particularly true when the guiding instrument comprises bone plate engagement features and/or locking features which secure onto screw holes of the bone plate, as described above. However, in certain embodiments, the guiding instruments (including the bone plate engagement features and, where applicable, the locking features) are designed taking into account the planned screw trajectories, such that the guiding instrument does not interfere with the trajectory of the screws for fixing the bone plate and does not need to be removed prior to screwing the bone plate.

Further, according to particular embodiments, the methods described herein may further comprise determining the optimal position and/or orientation of one or more drill guides.

Generating the guiding instrument may include designing a model of a guiding instrument or an image thereof. The design of the guiding instrument may further be provided on an information carrier or can be sent to a manufacturing facility for the manufacturing of the guiding instrument or parts thereof. Thus, in particular embodiments, the methods described herein include manufacturing the guiding instrument or parts thereof.

As detailed above, the methods described herein envision the generation of a guiding instrument comprising one or more surfaces that fit specifically with the bone fragment(s). In particular embodiments, the guiding instruments may comprise one or more free-form structures fitting at least part of the surface of the bone fragments. The term "free-form structure" as used herein refers to a structure having an irregular and/or asymmetrical flowing shape or contour, more particularly fitting at least part of the contour of the bone fragments. Thus, in particular embodiments, the free-form structure is a free-form surface, as described above. A free-form surface refers to an (essentially) 2D shape contained in a 3D geometric space. Indeed, as will be detailed below, such a surface can be considered as essentially 2D but may have a varying thickness. Typically, the free-form structure or surface is characterized by a lack of rigid radial dimensions, unlike regular surfaces such as planes, cylinders and conic surfaces. Free-form surfaces are known to the skilled person and widely used in engineering design disciplines. Typically non-uniform rational B-spline (NURBS) mathematics is used to describe the surface forms; however, there are other methods such as Gorden surfaces or Coons surfaces. The form of the free-form surfaces are characterized and defined not in terms of polynomial equations, but by their poles, degree, and number of patches (segments with spline curves). Free-form surfaces can also be defined as triangulated surfaces, where triangles are used to approximate the 3D surface. Triangulated surfaces are used in STL (Standard Triangulation Language) files that are known to a person skilled in CAD design. The free-form structures described herein are structured such that they fit the surface of the bone fragments specifically, thereby giving the structures their free-form characteristics.

Typically, the guiding instruments are designed to comprise free-form structures, wherein the free-form structures are patient-specific, i.e. they are made to fit specifically in the anatomy of a certain (animal or human) body-part.

Manufacturing the guiding instrument envisioned in the context of the methods described herein can involve methods that allow the generation of free-form objects according to a pre-determined design. In particular embodiments, the guiding instrument is manufactured at least partially by Additive Manufacturing (AM). If the guiding instrument comprises standard elements, e.g. standard locking means or plate engagement features, these may be made via other manufacturing methods, followed by assembly of the different elements of the guiding instrument.

Additive Manufacturing can be defined as a group of techniques used to fabricate a tangible model of an object typically using 3D computer aided design (CAD) data of the object. Currently, a multitude of Additive Manufacturing techniques is available, including stereolithography, Selective Laser Sintering, Fused Deposition Modeling, foil-based techniques, etc.

Selective laser sintering uses a high power laser or another focused heat source to sinter or weld small particles of plastic, metal, or ceramic powders into a mass representing the 3D object to be formed.

Fused deposition modeling and related techniques make use of a temporary transition from a solid material to a liquid state, usually due to heating. The material is driven through an extrusion nozzle in a controlled way and deposited in the required place as described among others in U.S. Pat. No. 5,141,680.

Foil-based techniques fix coats to one another by means of gluing or photo polymerization or other techniques and cut the object from these coats or polymerize the object. Such a technique is described in U.S. Pat. No. 5,192,539.

Typically AM techniques start from a digital representation of the 3-D object to be formed. Generally, the digital representation is sliced into a series of cross-sectional layers which can be overlaid to form the object as a whole. The AM apparatus uses this data for building the object on a layer-by-layer basis. The cross-sectional data representing the layer data of the 3-D object may be generated using a computer system and computer aided design and manufacturing (CAD/CAM) software.

The guiding instruments are thus typically made of material which is compatible with additive manufacturing and which is able to provide a sufficient stiffness to the free-form structure. Suitable materials include, but are not limited to polyurethane, acrylonitrile butadiene styrene (ABS), polycarbonate (PC), PC-ABS, polyamide, polyamide with additives such as glass or metal particles, methyl methacrylate-acrylonitrile-butadiene-styrene copolymer, resorbable materials such as polymer-ceramic composites, etc. Examples of commercially available materials are: DSM Somos® series of materials 7100, 8100, 9100, 9420, 10100, 11100, 12110, 14120 and 15100 from DSM Somos; ABSplus-P430, ABSi, ABS-ESD7, ABS-M30, ABS-M30i, PC-ABS, PC-ISO, PC, ULTEM 9085, PPSF and PPSU materials from Stratasys; Accura Plastic, DuraForm, CastForm, Laserform and VisiJet line of materials from 3-Systems; Aluminium, CobaltChrome and Stainless Steel materials; Maranging Steel; Nickel Alloy; Titanium; the PA line of materials, PrimeCast and PrimePart materials and Alumide and CarbonMide from EOS GmbH.

A further aspect relates to computer programs for carrying out the methods for generating the guiding instruments as disclosed herein. In particular embodiments, computer programs, which, when running on a computer, generate the guiding instruments as disclosed herein are provided. In particular embodiments the computer programs are adapted to perform the different steps of the methods described herein. In further embodiments, computer programs comprise software code adapted to perform the steps of the methods described herein. The data processing system or computer program particularly refer to computer aided design and manufacturing systems and programs such as CAD/CAM systems or programs. The computer programs typically comprise tools for loading images of the defective bone, tools for generating a 3D model of the bone based on the images, tools for generating a virtual element based on the 3D model and tools for designing the guiding instrument and optionally tools for instructing a manufacturing system to manufacture the guiding instrument according to the generated design.

The application further relates to guiding instruments for positioning a bone plate on at least one of two or more bone fragments. The guiding instruments may comprise a combination of one or more features which allow connection to a bone plate and one or more features which ensure correct positioning of the guiding instrument on one or more of the two or more bone parts. In particular embodiments, the guiding instruments are instruments, comprising: one or more patient-specific anatomy engagement surfaces or anatomy contact points corresponding to at least a part of one or each of the bone fragments; and one or more plate engagement features capable of connecting the guiding instrument to at least a part of the bone plate.

Indeed, the envisioned guiding instruments are designed to ensure a correct fit onto at least one of the bone fragments according to a preoperative plan (as described above) such that, when the bone plate is fixed to the bone fragments, correct positioning of the bone fragments relative to each other is ensured by the bone plate. In particular embodiments, the guiding instrument comprises two or more patient-specific anatomy engagement surfaces or anatomy contact points corresponding to at least a part of each of the bone fragments. In these embodiments, correct positioning of the guiding instrument onto the bone fragments will ensure correct positioning of the bone fragments relative to each other. In further embodiments, the guiding instrument comprises one or more patient-specific anatomy engagement surfaces or anatomy contact points corresponding to only one or not all of the bone fragments. In these embodiments, fixation of the bone plate to the bone fragments will fix the bone parts in the desired position relative to each other.

The structure of the guiding instrument may be such that the guiding instrument can securely be connected to the bone plate. However, in particular embodiments, the guiding instruments further comprise one or more locking features, optionally integrated into the one or more plate engagement features, which ensure a releasable locking of the guiding instrument to the bone plate. Embodiments of locking features are described above.

As detailed above, in further particular embodiments, the guiding instruments may comprise one or more (optionally removable) drill guides.

Additional features envisioned for the guiding instruments are described above, in the context of methods of manufacture, but are in no way limited by the methods of manufacture disclosed herein.

The guiding instruments disclosed herein are specifically adapted for connecting onto a bone plate. The nature of the bone plate is not critical as the structure of the guiding instrument can be adapted thereto. In particular embodiments however, the bone plate is a flat, longitudinal structure (i.e. aspect ratio of more than 2, more particularly more than 3). The bone-plate engagement features are typically characterized by a 3D structure which mates with part of the bone plate, which is typically the circumference of the bone plate. In most embodiments, the guiding instrument comprises at least one bone plate engagement feature which is a dedicated feature. In further particular embodiments, this feature comprises a groove fitting with the bone plate.

The present application further provides, kits or combinations are provided comprising a patient-specific guiding instrument as described herein and a bone plate, wherein the bone plate engagement features of the guiding instrument are designed to connect to the bone plate. As detailed above, in particular embodiments, the plate engagement features are features which are specifically adapted to the shape of the bone plate in order to ensure a releasable tight fit of the bone plate into the guiding instrument. In additional embodiments, the guiding instrument comprises two guide parts which, when connected, ensure a tight fit of the bone plate in the guiding instrument. Typically, the guiding instrument may comprise locking features which ensure a releasable grip with the bone plate. Further embodiments of the combinations of guiding instruments and bone plates are determined by the features described herein for the guiding instruments. Examples of bone plates for use in the combinations are described herein above.

In a particular embodiment a combination of patient-specific guiding instrument is provided with a bone plate, wherein the bone plate engagement features of the guiding instrument are designed to connect to recesses on the bone plate. In a particular embodiment, the bone plate is a Limited Contact Dynamic Compression Plate (LC-DCP) and the guiding instrument as described herein comprises one or more plate engagement features, such as a snap-fit system, designed to grip onto and/or behind one or more recesses of the LC-DCP, thereby attaching the bone plate onto the guiding instrument. In particular embodiments, the plate engagement features provide in a protrusion with an overhang or undercut between 0.2 mm and 5 mm, in particularly, between 0.5 mm and 2.5 mm, and more particularly about 1 mm.

Further embodiments relate to combinations of the guiding instrument with screws for fixing the guiding instrument onto the bone and/or with screw or drill guides.

The application provides methods for performing an orthopedic procedure, and more particularly for positioning a bone plate on at least one of two or more bone fragments, comprising the steps of: (i) providing a patient-specific guiding instrument as described herein (ii) connecting the guiding instrument to a bone plate; (iii) positioning the guiding instrument provided in step (ii) on the bone fragments via one or more anatomy engagement surfaces; (iv) fixating the bone plate onto the bone fragments; and (v) disengaging the guiding instrument from the bone plate.

In certain embodiments, the surgeon may be provided with a guiding instrument which is already connected to the bone plate via one or more plate engagement features provided on the guiding instrument. Alternatively, the surgeon receives the guiding instrument and bone plate separately, possibly from different suppliers as the bone plate can be a standard plate. Then, the surgeon connects the guiding instrument to the bone plate prior to positioning of the guiding instrument on the bone fragments. Optionally, the guiding instrument provided in step (i) is locked onto the bone plate via the locking features.

In certain embodiments, the guiding instrument is positioned onto the bone fragments, while still holding the bone plate. This is done by positioning the bone fragments relative to each other according to pre-operative planning and placing the guiding instrument on the bone fragments by way of the corresponding anatomy engagement features or contact points. Once the pre-operatively planned position is obtained, the surgeon may optionally fix the guiding instrument to one or more bone fragments via the fixation features described above.

In certain embodiments, the surgeon fixes the bone plate onto the bone fragments. Typically, this is obtained via pins or screws. If the bone plate is a locking plate, this is obtained via threaded screws fitting the threaded screw holes of the locking plate. Optionally, the surgeon may drill the screws into the bone via one or more drill guides provided on the guiding instrument.

In particular embodiments, the guiding instrument is removed from the bone fragments prior to fully fixating the bone plate onto the bone fragments. Alternatively, the guiding instrument is removed from the bone and the bone plate after the bone plate is fixed to the bone fragments. The step of removing the guiding instrument may involve releasing the locking features provided on the guiding instrument and/or detaching the two or more detachable guide parts of the guiding instrument from each other. If the surgeon has fixed the guiding instrument to the bone fragments in step (ii), step (iv) comprises removing the pins, wires, screws, etc. from the fixation features.

Optionally, where the bone plate is fixed to the bone prior to removal of the guiding instrument, the surgeon may further fix the bone plate to the bone fragments with additional screws or pins once the guiding instrument is removed. This may be required if one or more of the plate engagement features engage the plate in one or more of its screw holes. The screws that go into these screw holes will then have to be drilled after the guiding instrument has been removed.

When the orthopedic procedure involves one or more osteotomies, the present method is advantageously combined with some guided way of performing the osteotomy. This may be achieved by using patient-specific instruments, navigation or surgical robotics.

The following examples are provided for the purpose of illustration and by no means are meant and in no way should be interpreted to limit the scope of the present application.

EXAMPLES

Figure 1A:
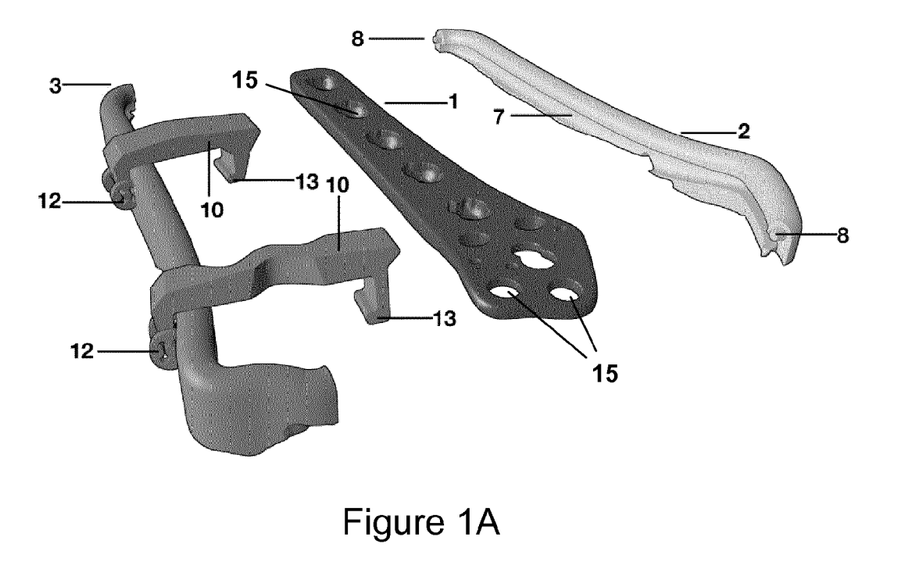
FIGS. 1A and 1B illustrate a guiding instrument (2, 3) according to a particular embodiment described herein, before connection to a bone plate (1).
Figure 1B:
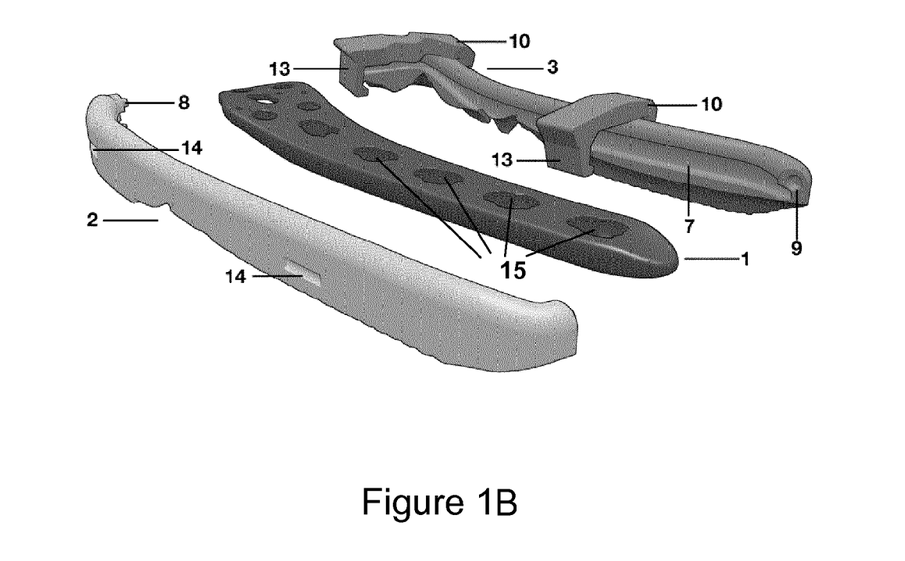

FIGS. 1A and 1B illustrate a guiding instrument (2, 3) according to a particular embodiment as described herein, before connection to a standard bone plate (1). The guiding instrument comprises two detachable guide parts (2, 3), which can be connected via pairs of matching alignment features (8, 9) and locking features (10). The locking features here comprise lever elements (10) which are connected at one end to the first guide part (3) via a hinge (12), whereby the other end of the lever element (13) is shaped to engage with a recess (14) the second guide part (2) of the guiding instrument, thus forming a snap-fit system. The guide parts each comprise a plate engagement feature (7) which connects the guiding instrument to the bone plate in a secure way. The bone plate comprises a plurality of threaded screw holes (15) allowing fixation of the bone plate to bones or bone fragments.

Figure 2:
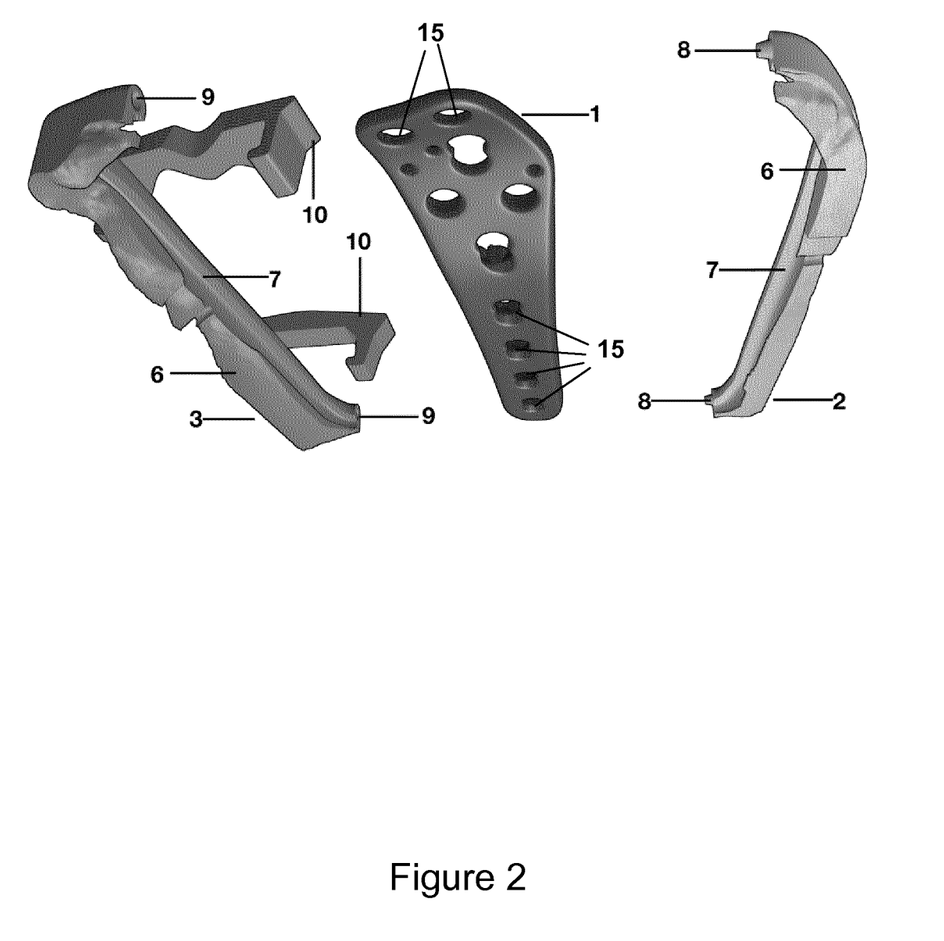
FIG. 2 shows a bottom view of a guiding instrument (2, 3) according to a particular embodiment described herein, before connection to a bone plate (1).

FIG. 2 illustrates a bottom view of the same guiding instrument (2, 3) and bone plate, and shows that the guide parts (2, 3) each comprise a patient-specific anatomy engagement surface (6), matching parts of the surface of two bone fragments (not shown).

Once the guide parts are connected to the bone plate via the plate engagement features and connected to each other via the alignment features, the guiding instrument can be locked via the locking means, such that the guiding instrument firmly holds the bone plate. This is illustrated in FIG. 3. FIG. 4 shows the same guiding instrument, not holding a bone plate.

Figure 5:
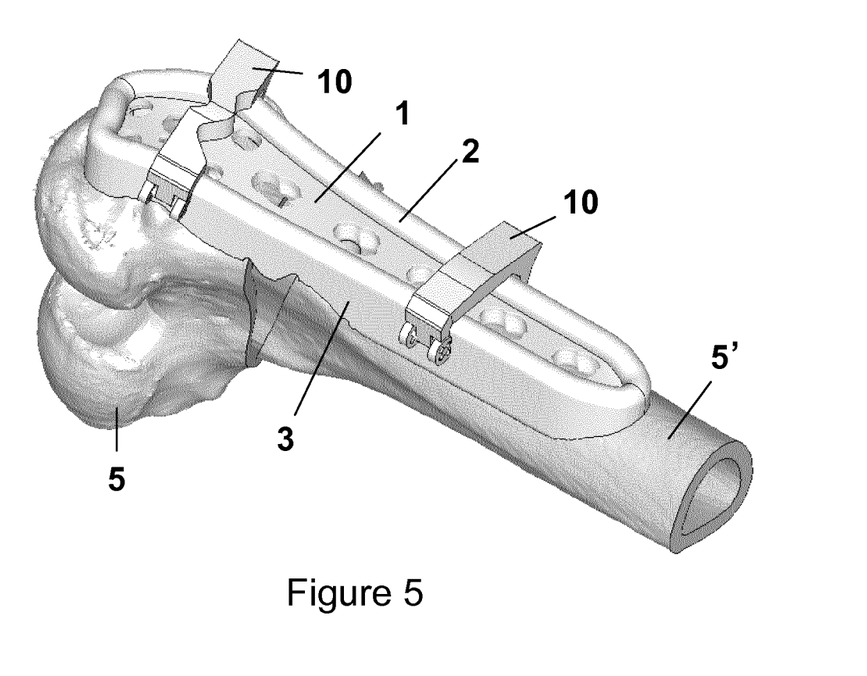
FIG. 5 illustrates a guiding instrument (2, 3) according to a particular embodiment described herein, connected to a bone plate (1) and positioned on two bone fragment (5, 5').

FIG. 5 illustrates the same guiding instrument (2, 3) when connected to the bone plate (1) via the plate engagement features (not shown) and positioned on two bone fragments (5, 5') via the bone engagement surfaces (not shown). By positioning the guiding instrument on the bone fragments, the bone fragments and bone plate are in the desired pre-operatively planned position.

Figure 6:
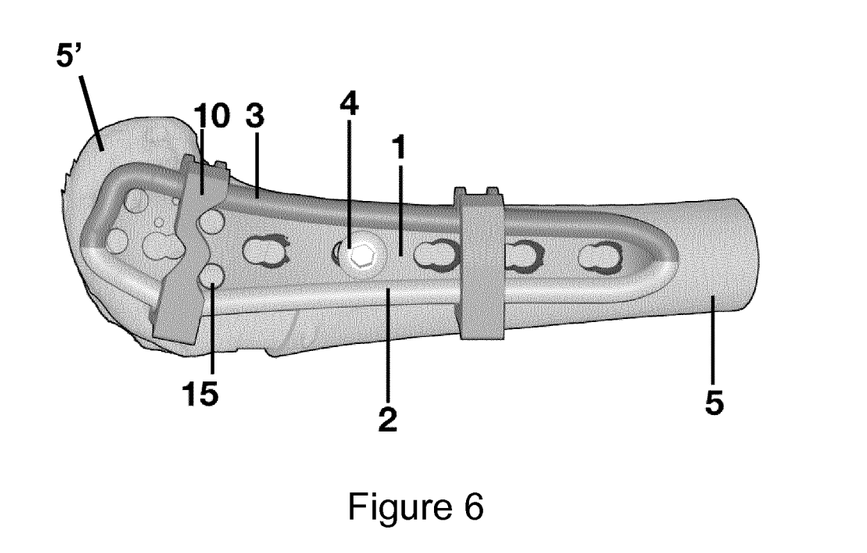
FIG. 6 shows a top view of a guiding instrument (2, 3) according to a particular embodiment described herein, connected to a bone plate (1) and positioned on two bone fragments (5, 5').
Figure 7:
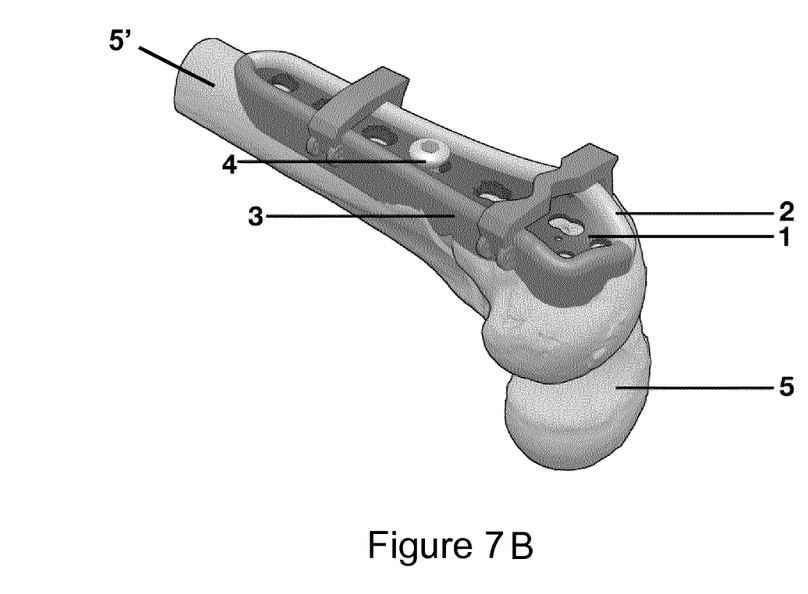
FIGS. 7A and 7B illustrate a guiding instrument (2, 3) according to a particular embodiment described herein, connected to a bone plate (1) and positioned on two bone fragments (5, 5').
Figure 7A:
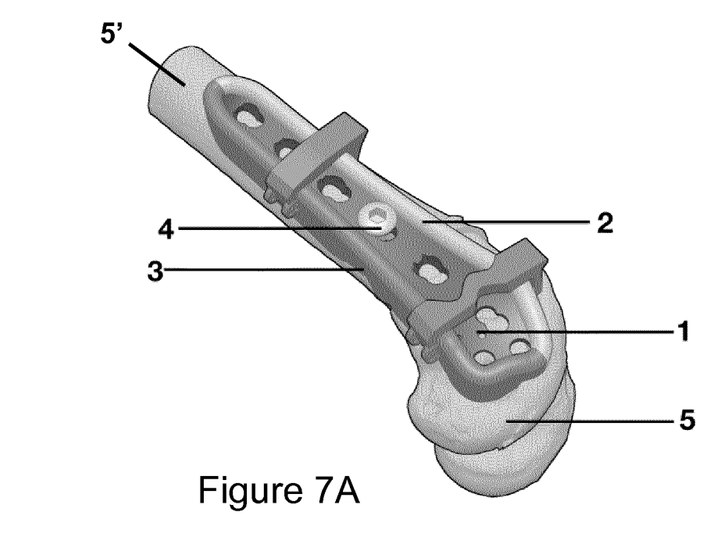

Once the desired position is obtained, the bone plate can be fixed to the bone via screws or pins. FIGS. 6, 7A and 7B show a guiding instrument (2, 3) as described herein holding a bone plate (1) positioned on two bone fragments (5, 5'). The bone plate is fixed to one of the bone fragments with a screw (4) via one of the screw holes (15) provided on the bone plate. The guiding instrument is designed such that it does not interfere with the trajectory of the screws. Indeed, the guide parts (2, 3) surround the bone plate such that any contact with the screws is avoided. Also the locking means (10) are shaped or positioned such that they do not interfere with the screw trajectory.

What is claimed is:

1. A patient-specific guiding instrument for positioning a bone plate on at least one bone fragment, comprising:
one or more guide parts, each of the one or more guide parts comprising:
at least one patient-specific anatomy engagement surface, wherein the at least one anatomy engagement surface matches a specific surface structure on the at least one bone fragment; and
one or more plate engagement features configured to connect the patient-specific guiding instrument to the bone plate, wherein the bone plate comprises one or more screw holes, and wherein at least one of the one or more plate engagement features of the guiding instrument is shaped to engaged at least one of the one or more bone plate screw holes.

2. The patient-specific guiding instrument according to claim 1, further comprising: one or more locking features configured to releasably lock the patient-specific guiding instrument onto the bone plate.

3. The patient-specific guiding instrument according to claim 2, wherein at least one of the one or more locking features is incorporated into at least one of the one or more plate engagement features.

4. The patient-specific guiding instrument according to claim 2, wherein at least one of the one or more locking features comprises: a dedicated feature configured to lock the patient-specific guiding instrument onto the bone plate by at least one of a snap-fit system or a threaded hole.

5. The patient-specific guiding instrument according to claim 1, wherein the patient-specific guiding instrument further comprises: one or more drill guides configured to guide at least one of a screw or a drill.

6. The patient-specific guiding instrument according to claim 1, wherein the one or more plate engagement features further comprise a structure configured to extend over at least part of a circumference of the bone plate, and wherein the structure includes a recess configured to fit the bone plate.

7. The patient-specific guiding instrument according to claim 1, wherein the at least one patient-specific anatomy engagement surface comprises a plurality of anatomy contact points which collectively correspond to the specific surface structure on the at least one bone fragment.

8. The patient-specific guiding instrument according to claim 1, wherein the patient-specific guiding instrument is manufactured at least partially by an additive manufacturing technique.

9. A patient-specific guiding instrument for positioning a bone plate on at least one bone fragment, comprising:
    one or more guide parts, each of the one or more guide parts comprising:
        at least one patient-specific anatomy engagement surface, wherein the at least one anatomy engagement surface matches a specific surface structure on the at least one bone fragment; and
        one or more plate engagement features configured to connect the patient-specific guiding instrument to the bone plate, wherein the guiding instrument further comprises two or more detachable guide parts, wherein at least one of the detachable guide parts comprises at least one of the one or more guide parts, and wherein each of the two or more detachable guide parts comprises one or more connecting features configured to uniquely connect the two or more detachable guide parts, the connecting features being one of an interlocking feature, a snap-fit system, a dovetail system, a pinned system, or a magnetic system.

10. A patient-specific guiding instrument for positioning a bone plate with respect to at least one bone fragment, comprising:
    one or more guide parts, each of the one or more guide parts comprising:
        at least one patient-specific anatomy engagement surface, wherein the at least one anatomy engagement surface matches a specific surface structure on the at least one bone fragment; and
        one or more plate engagement features configured to connect the patient-specific guiding instrument to the bone plate,
    wherein the one or more guide parts are configured such that when the one or more guide parts are positioned on the bone and when the bone plate is connected to the patient-specific guiding instrument by the plate engagement features, the bone plate has no direct contact with the at least one bone fragment.

* * * * *